(12) United States Patent
Shah et al.

(10) Patent No.: US 8,545,860 B2
(45) Date of Patent: Oct. 1, 2013

(54) BLOCK COPOLYMER AND ESTER-TERMINATED POLYESTERAMIDE COMPOSITION AND USES THEREOF

(75) Inventors: Arvind N. Shah, Suffern, NY (US); Freda E. Robinson, Nyack, NY (US); Kathy Cruz, Riverdale, NY (US); David Alan Binder, Saddle Brook, NJ (US); Prithwiraj Maitra, Randolph, NJ (US)

(73) Assignee: Avon Products, Inc., New York, NY (US)

( * ) Notice: Subject to any disclaimer, the term of this patent is extended or adjusted under 35 U.S.C. 154(b) by 80 days.

(21) Appl. No.: 12/645,919

(22) Filed: Dec. 23, 2009

(65) Prior Publication Data
US 2011/0150799 A1 Jun. 23, 2011

(51) Int. Cl.
*A61Q 1/08* (2006.01)
*A61Q 1/12* (2006.01)
*A61Q 5/00* (2006.01)
*A61Q 19/00* (2006.01)

(52) U.S. Cl.
USPC .......................... 424/401; 424/69; 424/70.11

(58) Field of Classification Search
None
See application file for complete search history.

(56) References Cited

U.S. PATENT DOCUMENTS

| 6,423,306 B2 * | 7/2002 | Caes et al. ................. 424/78.02 |
| 6,552,160 B2 * | 4/2003 | Pavlin ........................ 528/339.5 |
| 7,329,719 B2 | 2/2008 | Pavlin |
| 7,750,073 B2 * | 7/2010 | Brahms et al. ................ 524/506 |
| 2004/0202703 A1 * | 10/2004 | Meyer-Ingold et al. ...... 424/445 |
| 2005/0191327 A1 * | 9/2005 | Yu et al. ........................ 424/401 |
| 2007/0142521 A1 * | 6/2007 | Brahms et al. ................ 524/356 |
| 2008/0152679 A1 | 6/2008 | Brown et al. |

OTHER PUBLICATIONS http://www.in-cosmetics Jan. 27, 2012.*

* cited by examiner

*Primary Examiner* — Jyothsna Venkat
(74) *Attorney, Agent, or Firm* — David M. Joyal; Joan M. McGillycuddy

(57) ABSTRACT

Compositions and methods for the preparation of a composition comprising a block copolymer and ester-terminated polyester amide solubilized in a compatible solvent are disclosed. The disclosed compositions are long-lasting, transfer resistant, flexible, and water-proof capable of complexing the active ingredient to provide such benefits. The disclosed compositions are useful for formulating cosmetics, personal care products, cosmeceuticals, and the like.

6 Claims, No Drawings

BLOCK COPOLYMER AND ESTER-TERMINATED POLYESTERAMIDE COMPOSITION AND USES THEREOF

TECHNICAL FIELD

The present disclosure is in the field of cosmetic, personal care, and cosmeceutical compositions for application to skin, nails and hair and specifically relates to long lasting, transfer resistant compositions and uses thereof.

BACKGROUND

Film forming agents have long been employed to aid in spreading and adhering a cosmetic or personal care composition onto a surface, such as skin. However, many of these film forming compositions suffer from pressure sensitive tackiness and lack sufficient flexibility. In order to avoid these disadvantages, formulators would add fats or oils, such as glycerin, with various waxes to these film forming compositions, thereby resulting in the desired consistency of the product. However beneficial these conventional oily bases are in overcoming the disadvantages of the tackiness and inflexible properties, these benefits come at the cost of durability and transfer resistance. As such, conventional film forming cosmetics lack long wear and transfer resistant properties. It is therefore necessary to continuously re-apply the product, such as anhydrous products, powder products and the like, in order to maintain the desired coverage and natural effect.

Efforts to improve the durability and transfer resistance of cosmetic color products have focused on the use of polymeric film formers. For example, some lipstick compositions comprising volatile solvents, silicone resins, wax, powder and oil which are said to be transfer resistant while others utilize polyalphaolefins. However, efforts to provide a long wear, long lasting, transfer resistant, and good wear or comfortable product have met with only moderate success. For example, commercial lip products deemed to be transfer resistant have been reported to be uncomfortable to wear and may actually have a drying effect on the lips. Some disadvantages of using polyamide gellants alone include syneresis which is the extraction or expulsion of liquid from a gel or colloidal suspension. When a liquid forms, the resulting composition or film becomes dry and brittle. Waxes may be employed to provide structure, but they are typically not transparent nor translucent, but rather opaque, which is undesirable in the cosmetic arts for obtaining a natural appearance.

Block copolymers are generally employed in areas where the melt to solid transition property is less important, such as for example, footwear, wire insulation, adhesives, etc. More specifically, block copolymers are typically employed in applications where the polymer is heated above the melting temperature of the polymer's high melting domain. This renders the polymer liquid. As the polymer cools, the high melting domains form cross-links resulting in a network structure of physical cross-links, rather than the desired chemical cross-links. Such network structures form a swellable elastomeric structure that can be broken and reformed upon a temperature change. Other elastomeric structures are generally formed by chemical cross-links through, for example, condensation or free-radical chain transfer mechanism. These structures with chemical cross-links are not reversibly formed. Since block copolymers generally rely on the use of high heat, as the prior art suggests, their application to cosmetic and skin care products is not apparent and generally thought to be inappropriate.

There is a need in the art for cosmetic and personal products which are long wearing, comfortable, transfer resistant, and capable of maintaining the desired effect, such as but not limited to, color, moisture, and shine. It is therefore an object of the present disclosure to provide products, such as foundations, concealers, blushes, eye shadows, hair products, and the like which meet all of these requirements.

Despite advances in film forming methods and compositions, there remains a need in the art for film forming methods and compositions which provide long lasting, transfer resistant, comfortable, highly flexible, tack-free, abrasion resistant, and water and oil resistant films that through their unique properties, maintain and prolong the desired effect, such as but not limited to color, moisture, and shine.

It is a further object of the disclosure to provide cosmetic, personal care, and cosmeceutical compositions which form a long lasting, non-tacky, flexible, water and oil resistant, abrasion resistant, and transfer resistant film and deliver actives, colorants, and the like for a natural, fresh looking appearance.

SUMMARY

In accordance with the foregoing objectives and others detailed herein, the disclosed composition overcomes deficiencies associated with the prior art by providing in one embodiment, compositions comprising at least a block copolymer and a modified modified polyester amide, that form a stable, homogeneous gel or solution without any observable particulate matter and without syneresis.

A more specific embodiment is directed to a composition that comprises a charge-neutral hydrophobic block copolymer and an ester-terminated polyesteramide (ETPEA) polymer dissolved in a solvent or solvents, which forms a stable, translucent, homogeneous gel or solution without any observable particulate matter and without syneresis that is long lasting, transfer resistant, sweat proof, humidity proof, water resistant, oil resistant, abrasion resistant, flexible, durable, natural and fresh looking, fresh feeling, comfortable, easily spreadable with minimal tackiness, provides flawless aesthetics, and/or maintains or prolongs the desired effect. The biological surface may be any surface to which cosmetics, personal care products, and cosmeceutical compositions are typically applied, including but not limited to skin, lips, hair, nails, and the like. The resultant film that forms after application is durable, flexible, water and oil resistant, abrasion resistant, transfer resistant, and long lasting.

Another embodiment provides a method of preparing and using the disclosed composition which is a stable, homogeneous gel or solution without any observable particulate matter and without syneresis.

A further embodiment is directed to cosmetic, personal care, or cosmeceutical compositions comprising the disclosed composition and additional ingredients depending on the specific application.

These and other aspects of the present disclosure will become apparent to those skilled in the art after a reading of the following detailed description, including the illustrative embodiments and examples.

DETAILED DESCRIPTION

The inventive composition comprises a block copolymer and a polyesteramide that has been modified where both the block copolymer and modified polyesteramide are uniformly and homogenously solubilized in a compatible solvent or mixture of solvents.

More specifically, the solubilized block copolymer and an ester-terminated polyesteramide (ETPEA) polymer form a stable, homogeneous gel or solution without any observable particulate matter and without syneresis. The composition may be topically applied to biological or keratinous tissue, including but not limited to skin, nails, and hair, of a mammal, such as but not limited to a human, canine, feline, equine, murine, rodents, and the like. Although block copolymers have been used alone or in combination with resins in conventional compositions, a block copolymer and an ETPEA as disclosed here was surprisingly found to have superior long wear, transfer resistant, comfort and natural looking properties that maintain or prolong the desired effect.

Without being bound by theory, the block copolymer and ETPEA gel or solution of the disclosed composition strongly complexes with organic molecules such as for example, but not limited to, pigments, ultraviolet absorbers, actives or drugs, shine enhancers, long wear ingredients, for delivery to the biological surface to which the composition is applied. For compositions such as cosmetics, personal care products and cosmeceuticals, the ability to hold onto specific ingredients is extremely beneficial as oftentimes the effects of compositions such as those found in the prior art are temporary and lack endurance. This is particularly useful for maintaining, retaining, or prolonging, for example, color in colored cosmetics, ultraviolet protection in sunblocks, moisture in lotions or creams, and shine enhancers or conditioning materials in hair products.

Desirable characteristics of the composition include, but are not limited to: goad/ease of application, the production of a uniform film, good adhesion, a certain amount of flexibility, and good film strength to avoid cracking and flaking of the film, preferably without irritating the skin, hair, and/or nails or other keratinous surfaces upon which the composition is applied. The composition also, in particular, presents long and good wear properties, transfer resistance, sweat/humidity proof, natural and fresh looking, flawless appearance, and where desired, smooth texture and spreadability. More particularly, the inventive compositions provide a unique benefit that allows for holding, maintaining, or prolonging a desired effect or property, such as but not limited to, color, moisture, shine, conditioning, sun blocks or sunscreens, insect repellants, anti-aging actives, and the like.

One embodiment of the disclosure encompasses a composition which comprises a block copolymer that is particularly useful as a film former, and an ETPEA, where the selected block copolymer and ETPEA have compatible solubilities such that they solubilize to form a stable, homogenous gel or solution without any observable particulate matter and without syneresis. The block copolymer in the composition of the instant disclosure is charge-neutral and hydrophobic. While natural and synthetic polymers and mixtures thereof have been useful as film formers in cosmetic compositions, charge-neutral hydrophobic block copolymers are particularly beneficial in forming a flexible, water and oil resistant, abrasion and transfer resistant, non-shrinking, non-tacky, and comfortable film.

The combination of block copolymers and modified polyamides, in particular, ester-terminated polyester amides (ETPEAs), provide for the surprising enhancement of the long wearing properties found in block copolymers alone. This combination ultimately improves the wear properties, spreadability and flawless aesthetics of the composition. Without being bound by theory, the high cohesive strength provided by a block copolymer must be combined with an ingredient allowing for chain mobility and adhesion to a substrate. Tackifier resins and oil bases as used in other conventional compositions assist to some degree, but these combinations result in a tacky pressure-sensitive composition or lack the durability and transfer resistance highly desirable in a cosmetic, personal care, or cosmeceutical composition. Whereas, the block copolymer and ETPEA of the disclosed composition described herein provides superior benefits such as transfer resistance and durability without the tackiness and yet maintains good wear properties as well as maintaining a strong hold onto moisturizers, shine enhancers, actives, colorants, pigments, and the like.

Generally, block copolymers are multiphase compositions where at least one phase has a material that is hard at room temperature, but becomes fluid or less hard upon heating, i.e., the hard phase or domain. Another phase of the block copolymer has a material that is softer, more like rubber at room temperature, i.e., the elastomer phase or domain. The block polymer of the disclosure may have any form of diblock, triblock, multi-block copolymer or combinations thereof. For example, useful block copolymers having a hard domain or block A (high Tg block) and a soft, elastomer domain or block B (low Tg block) include an A-B diblock copolymer, an A-B-A tri-block copolymer, such as poly(styrene-b-elastomer-b-styrene), styrene-isobutylene-styrene (SIBS), styrene-silicone-styrene, and a multi-block copolymer structure (A-B)n, as well as branched block copolymers having a structure of (A-B)nx (where x represents an n functional joint). More specifically, in addition to the aforementioned examples, non-limiting block copolymers include polyurethane/elastomer block copolymers, polyester/elastomer block copolymers, polyamide/elastomer block copolymers, polyethrimide/polysiloxane block copolymers, and any combinations thereof. Block copolymers useful in the composition described herein are preferably A-B-A triblock copolymers alone or in combination with other block copolymers, such as for example, an A-B diblock copolymer.

In another embodiment, the block copolymer is a linear A-B-A triblock type, such as but not limited to, styrene-butadiene-styrene, styrene-isoprene-styrene, or styrene-ethylenebutylene-styrene. As one skilled in the formulation art understands, diblocks generally provide softness properties while triblocks provide hardness properties to a film. Another embodiment is directed to the combination of diblocks and triblocks. More preferably, the block copolymer used in the composition of the disclosure is a styrene-isobutylene block copolymer, such as styrene-isobutylene-styrene (SIBS) as found in the commercialized product SIBSTAR® (Kaneka Corporation; Houston, Tex.). As will be understood, additional examples of suitable block copolymers and methods of preparing them are available in U.S. Publication No. 2007/0142521.

Block copolymers useful in the inventive composition have a high molecular weight. For example, the block copolymers have an average molecular weight between about 100,000 and about 113,000 Daltons with a molecular weight distribution below 2.

A further embodiment of the inventive composition comprises components, including the block copolymer, that provide for a solid-gel (sol-gel) transition temperature (Tgel) that is typically above about 40° C., more typically, above about 50° C., above about 60° C., and most typically above about 70° C. In an exemplary embodiment, the block copolymer has a $T_{gel}$ between about 70° C. and about 85° C., including representative embodiments having a $T_{gel}$ of about 70° C., about 75° C., about 80° C., and about 85° C. Thus, enabling the inventive composition comprising the disclosed block copolymers and ETPEAs to remain gelled during wear, i.e., when applied to the skin or hair, and during storage under ambient conditions. As the skilled formulator understands, the properties of the block copolymers and ETPEAs useful in the disclosed composition are compatible to such a degree that enables the production of a stable, homogenous gel without any observable particulate matter and without syneresis. For example, the Tgel of the block copolymer must be compatible with the Tgel of the ETPEA and are selected accordingly to avoid a block copolymer that has a Tgel significantly higher than that of the ETPEA such that they could not be combined to form the desired composition. Another property that is useful to consider when selecting the components of the inventive composition is the softening point. Each component has a temperature at which the material softens beyond some arbitrary softness. In order to maintain the structure of the inventive composition, the block copolymer and ETPEA should have softening temperatures that are similar. In some embodiments, the softening point of the block copolymer ranges from about 70° C. to about 100° C. and about 80° C. to about 90° C.

The film forming block copolymers used according to the disclosure have a glass transition temperature (Tg) in a range which causes a soft and elastic film to be produced. Glass transition temperatures are the point at which the polymer or fragment thereof moves from a solid brittle state into a rubbery liquid state. As will be understood by one skilled in the art, in order to understand this concept and to identify particular combinations of polymers or hard and elastomer phases, which would be useful in the disclosure, the Tg of various polymers may be determined through testing and by referring to the glass transition points which are described and disclosed in commonly known and used references (see, *Polymer Handbook*, Eds. J. Brandrup, et al., 2 Volumes Set, Fourth Edition, John Wiley and Sons, Inc., June 2003; *Introduction to Polymer Science and Technology*, Eds. H. S. Kaufman and J. J. Falcetta, John Wiley and Sons, Inc., 1977).

In a further embodiment, any charge-neutral, non-polar, hydrophobic block copolymer may be used in the disclosed composition, where the hard phase, for example, has a glass transition temperature (Tg) of about 40° C. or greater, about 50° C. or greater, or about 60° C., and the elastomer phase, has a Tg less than about 25° C., about 10° C. or lower, or about 0° C. or lower. Yet a further embodiment encompasses a block copolymer where the two phases differ in Tg by about 15° C., by about 30° C., or by about 50° C. These characteristics enable the composition to be non-tacky, flexible, and comfortable.

In yet another embodiment, ester-terminated polyesteramides (ETPEAs) are used to complement the high cohesive strength provided by the block copolymers with the chain mobility and adhesive properties of the ETPEAs which are important for obtaining and maintaining long lasting wear and transfer resistant properties. Any ETPEA compatible with the block copolymer for cosmetic, personal product, and cosmeceutical use is contemplated to be suitable, provided the block copolymer and ETPEA are capable of existing as a gel or solution at room temperature and, further, at body temperature, and the gel or solution is stable and homogenous without any observable particulate matter and without syneresis.

In the broadest scope, almost any ester-terminated polyester amide may be useful in the inventive composition if compatible with the block copolymer to form a stable, homogeneous gel or solution without any observable particulate matter and without syneresis for use in a cosmetic, personal care, or cosmeceutical composition. Examples of polyamides of polycarboxylic acids containing esterified carboxyl groups or ETPEAs are found and described in U.S. Pat. Nos. 3,141, 787; 6,552,160; 6,875,245; 7,253,249; and 7,329,719. Generally, ETPEAs in the instant composition also provide conditioning and protection for skin or hair as emollients while controlling viscosity.

In one embodiment, the ETPEA is a bis-di-$C_{14-18}$ alkyl amide or a copolymer of ethylenediamine, neopentyl glycol and hydrogenated dilinoleic acid end-blocked with stearyl alcohol, having an International Nomenclature of Cosmetic Ingredients (INCI) name of bis-stearyl ethylenediamine/neopentyl glycol/stearyl hydrogenated dimer dilinoleate copolymer. Non-limiting examples of ETPEAs are also disclosed in U.S. Pat. No. 7,329,719 and U.S. Publication No. 2008/0152678. For example, a useful ETPEA of the disclosure is prepared from co-diamine, where the co-diamine is, but not limited to, 1,6-hexanediamine, xylenediamine, 1,2-propanediamine, 2-methylpentamethylenediamine, or 1,12-dodecanediamine. Suitable diamines of the present disclosure are available from commercial sources including, but not limited to, Aldrich (Milwaukee, Wis.); EM Industries, Inc. (Hawthorne, N.Y.); Alfa Aesar (Ward Hill, Mass.); and Spectrum Quality Product, Inc. (New Brunswick, N.J.). A commercialized ETPEA product that is readily available is SYLVACLEAR® C75V (Arizona Chemical; Jacksonville, Fla.). The ETPEA has a hydrophobic property that provides the benefit of water resistance and enhancing gloss or sheen. When the ETPEA is solubilized with low polarity liquids or solvents, the benefits that result include a unique feeling, shear thinning, and excellent payout. Another benefit of the ETPEA is that it may be modified depending on the application. For example, ETPEAs may be used to make solid, gels, solutions, or emulsions.

Generally, the ETPEAs useful in the inventive compositions have a low molecular weight, blend easily into formulations, and provide a soft feel on the skin or hair. They have little color if any color and have no odor. ETPEAs have a melting point ranging from about 70° C. to about 80° C. They have an average molecular weight between about 3000 Daltons and about 6000 Daltons, where in one embodiment, the ETPEA has a molecular weight of about 4500 Daltons.

In one embodiment, increasing the average molecular weight for the ETPEA tends to increase the melting point and melt viscosity of the ETPEA which relates to a firmer gel when combined with a low polarity solvent. However, EPTEAs become insoluble in low polarity solvents if the average molecular weight is too high and should be selected to avoid such circumstances. The selected ETPEA, however, will be compatible with the selected block copolymer and maintain a stable, homogeneous gel without any observable particulate matter and without syneresis at room temperature and at body temperature. Selection is also based on their sol-gel transition temperatures $T_{gel}$ and the melting points of both components being above room temperature (about 23° C.) and preferably above body temperature (about 36° C. to about 38° C.).

Typically, the ETPEAs of the inventive composition have a low melting point (<100° C.) and do not sensitize skin or hair which is similar for the disclosed block copolymers. ETPEAs generally contain lipophilic elements only, and without polyether elements in the chain. Because of these elements, ETPEAs form transparent, soft yet firm solids with fats/oils, low polarity emollient esters and low-HLB surfactants but are incompatible with ketones, polar ethers and glycols. They are excellent for wetting and stabilizing pigments and are useful for providing water repellency to mascaras and sunscreen formulations. The solid-gel (sol-gel) transition temperature Tgel of the ETPEA polymer is typically above about 40° C., more typically, above about 50° C., above about 60° C., and most typically above about 70° C. In an exemplary embodiment, the ETPEA has a $T_{gel}$ between about 70° C. and about 85° C., including a representative embodiments having a $T_{gel}$ of about 70° C., about 75° C., about 80° C., and about 85° C. The inventive composition comprises block copolymers and ETPEAs which remain gelled or in solution during wear, i.e., when applied to the skin or hair, and during storage under ambient conditions.

The temperature at which a material softens beyond some arbitrary softness (Petrie, Edward (2006). *Handbook of Adhesives and Sealants*. McGraw-Hill. p. 146), also known as the softening point, may be measured by, for example, differential scanning calorimetry (DSC). The softening point of the ETPEA polymer will also be useful for approximating the sol-gel transition temperature $T_{gel}$ as this is the point where the hydrogen bonding network of the polymer gel begins to break down. In some embodiments, the softening point of ETPEA ranges from about 70° C. to about 100° C. and about 80° C. to about 90° C.

As would be understood by one skilled in the art, residual tackiness of a composition at room temperature and at normal atmospheric pressure may be adjusted by selecting a suitable ETPEA. The Tg and the compatibility of the ETPEA are the major factors controlling the adhesive properties of the disclosed block copolymer/ETPEA combination. Tg has a relationship with softening point and it is more useful for formulators to be aware of the Tg value than the softening point value of a ETPEA for formulation purposes. As an example, use of the correct Tg ETPEA and the right ETPEA concentration in a polymer composition provide the desired properties. Preferred ETPEAs have a Tg between about −60° C. and about 200° C., preferably between about −40° C. and about 170° C., and most preferably between about −30° C. and about 150° C.

Solubility parameters also provide a numerical method of predicting the interaction between materials, such as liquids and polymers. They are useful in determining the suitability of polymers for particular applications and in formulating mixtures of solvents for specific purposes. A further embodiment of the disclosure relates to solubility parameters between the two phases or domains of the block copolymer and/or between each of the phases and the volatile solvent or mixtures thereof. One of ordinary skill in the art may be able to determine the solubility parameters and choose a solvent based on the block copolymer and ETPEA chosen for the envisaged application. More information regarding solubility parameters and solvents useful in the processing of specific block copolymers and ETPEAs are available from the various manufacturers of such polymers. Additional discussions of polymer solubility parameter concepts are presented in: *Encyclopedia of Polymer Science and Technology*, Vol. 3, Interscience, New York (1965) and *Encyclopedia of Chemical Technology*, Supp. Vol., Interscience, New York (1971), the disclosures of which are all hereby incorporated by reference.

In a further embodiment which is particularly suitable for achieving the particularly good properties of the inventive composition, the block copolymers have a difference in solubility parameter between the hard phase and the elastomer phase of at least 0.5 (cal/cc)½. In one embodiment, the ETPEA has a solubility parameter within about 1 (cal/cc)½, preferably within about 0.5 (cal/cc)½, and more preferably within about 0.2 (cal/cc)½ of each of the elastomer phases of the block copolymer in a composition. In another embodiment, the ETPEA has a solubility parameter within about 1 (cal/cc)½, preferably within about 0.5 (cal/cc)½, and more preferably within about 0.2 (cal/cc)½ of each of the hard phases of the block copolymer in a composition. In another embodiment, the ETPEA has a solubility parameter within about 0.2 (cal/cc)½ of that of the block copolymer, preferably its hard phase. In yet a further composition, the ETPEA has a solubility parameter within about 0.2 (cal/cc)½ of the elastomer phase of the block copolymer.

As will be understood by those of skill in the art, the solubility parameters for the block copolymer phases and solvents or mixtures thereof may be determined, by referring to commonly known and used references, in order to form compositions of the disclosure. (see, for example, Allan F. M. Barton, *Handbook of Solubility Parameters and Other Cohesion Parameters*, Second Edition, CRC Press, Boca Ratan, Fla., 1991; Hansen, Charles M., "The Three Dimensional Solubility Parameter—Key to Paint Component Affinities: I. Solvents Plasticizers, Polymers, and Resins," *Journal of Paint Technology*, Vol. 39, No. 505, 1967; Hansen, Charles M., "The Three Dimensional Solubility Parameter—Key to Paint Component Affinities: II. Dyes, Emulsifiers, Mutual Solubility and Compatibility, and Pigments," *Journal of Paint Technology*, Vol. 39, No. 511, 1967; Hansen, Charles M., "The Three Dimensional Solubility Parameter—Key to Paint Component Affinities: Ill. Independent Calculations of the Parameter Components," *Journal of Paint Technology*, Vol. 39, No. 511, 1967).

The preferred solvents depend on the particular block copolymers and ETPEAs used in the disclosure. The solvent may be used in conjunction with one or more additional solvents conventionally used in compositions as are well known in the art. The particular solvents may be selected from volatile or non-volatile solvents. Non-limiting examples of preferred solvents include non-polar or low polarity solvents that are compatible with the film forming block copolymers and ETPEAs present in the composition in amounts which facilitate the temporary breakage of the physical cross-links and sufficiently solubilize the block copolymers and ETPEAs to allow the physical cross-links to reform creating a durable, long wearing, transfer resistant film. Typically, the topical composition of the disclosure comprises an acceptable solvent or a mixture of solvents in addition to the block copolymer and ETPEA, enabling the composition to retain its gel, liquid, or semi-solid form.

In one embodiment with respect to the solvent portion of the composition, at low concentrations of block copolymers and ETPEAs, such as less than or equal to about 5 weight % in a composition, the composition must have a volatile solvent or mixture thereof that is compatible with the ETPEA and at least the elastomer domain of the block copolymer. This composition may optionally also have additional solvents including one or more volatile or non-volatile solvents. Furthermore, the solvent or mixture thereof may be compatible with the hard domain of the block copolymer. Whereas, at high concentrations of block copolymers and ETPEAs, such as more than or equal to about 5 weight % in a composition, the composition must have a volatile solvent or mixture thereof that is compatible with the ETPEA and at least the hard domain of the block copolymer. This composition may optionally have a volatile or non-volatile solvent, or combinations thereof, that are compatible with the soft domain.

The amount of solvent, including solvent mixtures as set forth above, necessary to ensure an acceptable product viscosity (i.e., ease of applying without being runny) depends on the nature of the solvent and the nature and amounts of the other ingredients, such as, in particular block copolymers and ETPEAs. The amount of solvent may be readily determined by routine experimentation.

Non-limiting examples of solvents useful in the compositions described herein include, isododecane, isohexadecane, isopropyl palmitate, myristyl palmitate, hexane, cyclohexane, toluene, dichloromethane, aliphatic, olefinic and aromatic hydrocarbons, chlorinated hydrocarbons, ketones, acetates, ether, chloroform, esters, silicones and combinations thereof. Solvents not found useful in the composition because the block copolymers may not dissolve include, but are not limited to, tetrahydrofuran; methylethylketone; acetone; dimethyl formamide; N,N-dimethylacetamide; methanol; and ethanol. The skilled practitioner understands how to select the appropriate solvent for solubilizing the block copolymer and ETPEA of the inventive composition.

As will be understood by those of skill in the art, the solvent and solubility conditions may be altered in order to prepare a composition which has the desired properties. The skilled practitioner will further appreciate the solubility parameters, Tgel, Tg, softening points, and the like, which can be approximated by the formulas known in the art, and depending on the block copolymer, ETPEA, solvent, and other ingredients and conditions of the inventive composition.

In a preferred embodiment, the composition of the instant disclosure relates to a composition comprising a charge-neutral hydrophobic block copolymer, an ETPEA, and a solvent or a mixture thereof which dissolves the block copolymer and ETPEA, forming a stable, translucent, homogeneous gel without any observable particulate matter and without syneresis. The resulting film surprisingly overcomes known disadvantages by producing a film having properties such as good adhesion, stability, flexibility, wearability, non-tackiness, good retention, transfer resistance, abrasion resistance, and low migration overtime.

For the inventive composition comprising the block copolymer and ETPEA, the effective amounts for each range from about 0.01% to about 50%; about 0.05% to about 25%; and about 0.1% to about 10%. More particularly, the disclosed compositions comprise a block copolymer of about 0.1% to about 6%; about 0.5% to about 4.5%; and about 1% to about 4%; and an ETPEA having a weight percent from about 0.0.01% to about 5%; about 0.05% to about 1%; and about 0.1% to about 0.7%; and solvent in an amount ranging from about 10% to about 90%; about 13% to about 88%; about 35% to about 70%; and about 47% to about 56%. In general, the amount of solvent suitable for the purpose of this disclosure falls in the range of from about 1% to about 90% by weight of the composition, about 5% to about 80% by weight of the composition, and about 10% to about 30% by weight of the composition.

In one embodiment of the disclosure, the composition as described herein is useful as a gel which is stable and self-supporting at room temperature. Depending on the application, the composition is preferably clear or translucent in order to allow the active ingredient, such as a pigment for a foundation, to provide its intended color without adjustment which may be necessary if the composition itself is colored. Alternatively, a clear gel comprising the block copolymer and ETPEA dissolved in solvent may preferably be used as, for example, a primer alone or underneath any colored make up, a clear gel personal care product, such as an anti-perspirant or an anti-deodorant, or a clear hair product.

One embodiment is directed to the preparation of the gel or solution composition of the disclosure, the block copolymer and ETPEA are completely dissolved in a solvent or mixtures thereof, which is not limited to volatile or non-volatile solvents, although preferably low polarity or non-polar. More specifically, the method of making the disclosed composition generally occurs by dissolving the block copolymer and ETPEA in solvent, mixing, heating, and cooling. In one embodiment, the block copolymer and ETPEA may first be mixed and dissolved in solvent and then incorporated with other ingredients or actives commonly found and used in a cosmetic, personal product or cosmeceutical composition.

In particular, the block copolymer and ETPEA of the disclosure are dissolved in a compatible solvent or mixture of solvents including but not limited to, for example, isododecane, hydrogenated polyisobutene, isohexane, isohexadecane, isoeicosane, isopropyl palmitate, myristyl palmitate, and the like, or combinations thereof. All of these ingredients are mixed at a speed of about 500 rpm to about 2500 rpm in a sealed jacketed mixing chamber and heated at about 95° C. for about three to about six hours using a programmable heating unit or until all ingredients are uniformly dissolved. The mixture is then cooled down to a temperature ranging from about 71° C. to about room temperature 25° C. with slow mixing of less than about 500 rpm. The block copolymer and ETPEA mixture and method of making is exemplified in Example 1. In certain embodiments, the inventive composition is formulated into foundations, pressed powders, and lip and eye compositions as described in Examples 2 to 4.

The preparation of a foundation composition is more specifically detailed in Example 2. However, briefly, the amounts useful in such a formulation exemplified in Table 2 may have the following ranges, by weight of the total composition. Phase A comprising the block copolymer and ETPEA gel or solution is in an effective amount ranging from about 0.1% to about 50%; about 0.1% to about 40%; and about 1% to about 25%. The solvents, emulsifiers and the like of Phase B are present in an amount totaling about 0.1% to about 50%; about 0.1% to about 40%; and about 1% to about 25%. Table 3 is directed to a foundation composition further comprising phenyl trimethicone in a total amount ranging from about 0.5 to about 10% and about 1% to about 5%.

Phase C of the compositions described in Tables 2 and 3 may be further divided with respect to the application. In one embodiment where a non-colored final formulation is desired, Phase C comprises fillers, microspheres, and non-colored pigments (or without any pigments or colorants) present in an effective amount ranging from about 0.1% to about 45%; about 1% to about 40%; and about 1% to about 25%. Whereas, another embodiment where color is desired, for example, to provide multiple shades of color to match various skin tones, Phase C may comprise colored pigments added in amounts ranging from about 0.1% to about 20%; about 0.1% to about 15%; and about 0.1% to about 10%.

In another embodiment, a pressed powder formulation is also provided that achieves the comparable desired long lasting and durable effects as those found in the inventive foundation composition. Specifically, Table 4 of Example 3 exemplifies the effective formulations falling within the acceptable ranges disclosed herein. The block copolymer of Phase A is in an amount ranging from about 0.01% to about 20%; 0.1° A) to about 10%; and about 0.1% to about 7%. While the amount of ETPEA may be even less, an amount to the total formulation ranging from about 0.01% to about 10%; about 0.01% to about 7%; and about 0.1% to about 5%. The solvents of Phase B are in an amount sufficient to solubilize the aforementioned ingredients to form a homogenous mixture. Specifically, the solvents are in an amount ranging from about 0.1% to about 50%; about 0.1% to about 25%; and about 0.1% to about 20%. The fillers and microspheres of Phase B may be present in a range from about 1% to about 90%; about 20% to about 90%; and about 50% to about 85%. The pigments of Phase B which may be colored or non-colored, total in a range from about 0.01% to about 20%; about 0.1% to about 15%; and about 0.1% to about 10%.

A further embodiment is directed to the lip and eye compositions exemplified in Example 4. The disclosed lip and eye compositions complex to the colorants or pigments thereby enabling particularly long lasting color. These compositions are especially useful because the lip and eye areas tend to lose the product and the effects, such as color, due to, for example, the high frequency of movement, i.e., puckering, blinking, etc. As exemplified in Tables 5-8, these formulations may be either gel or stick compositions.

In another embodiment, the disclosed composition may be formulated into a hair care product. The hair composition may be a shampoo, a conditioner, a leave in conditioner, a hair colorant, a shine enhancer, a defrizzing conditioner, and the like. The hair product of the disclosure is advantageous over the conventional hair products found in the art and prolongs the desired effect on the hair. Non-limiting examples of the desired ingredients that are complexed to the disclosed hair care composition include shine enhancing, color maintaining, defrizzing, or antistatic active ingredients to form a long lasting film forming a barrier on the hair. See Examples 5 and 6 for exemplary hair product compositions.

Other embodiments are directed to the method of preparing the hair compositions of the disclosure. In particular, Phase A comprising the block copolymer, the ETPEA, and the solvent combined together with emollients and conditioning materials are heated at a temperature ranging from about 110° C. to about 130° C., and about 116° C. to about 120° C. in, for example, a mineral bath, and mixed at medium speed until uniformly dissolved. Once Phase A is cooled to a temperature ranging from about 70° C. to about 25° C. or room temperature, the ingredients of Phase B are added and mixed at about 60° C. to about 70° C. and at slow speed until uniformly mixed and dissolved.

Example 7 provides the results of a consumer survey. After application of both the inventive foundation formulation and the leading long lasting/wearing foundation ("Standard"), the consumers found that the inventive composition or "Combined foundation" was not only longer lasting but also provided more comfort overall when compared to the Standard. The Combination foundation was also deemed to even out skin tone, reduce the appearance of redness, wrinkles and age spots. Example 8 is directed to consumer testing of the disclosed foundation composition. Overall, the results provided that consumers found that the product provided similar benefits after initial application and 8 hours later. Further evidence of one of the benefits of the foundation is demonstrated in Example 9 which is directed to the comparison of the inventive foundation product to other foundations with respect to transfer resistance.

In order to develop better hair products that enhance shine, several approaches have been used over the last 5 or 6 years to measure shine. Subjective measurements may be taken by trained evaluators, gloss meters that work better for flat surfaces versus lips or hair, and equipment for image analysis. One of the advantages the image analysis technique described in Example 10 is that there is no limitation to flat surfaces and shine may be measured 'instantly' in real time. An article featured by Cosmetics and Toiletries Magazine, "*In Vivo Quantitative Evaluation of Gloss*," October 2004, features the Bossa Nova instrument and shine methodology. ISP, International Specialty Products, an ingredient manufacturer has also published work using image analysis technique to quantitative shine. Example 10 presents the increase in shine of hair treated with the disclosed hair product compared to untreated hair.

Yet a further embodiment of the disclosure is directed to the use of the inventive composition in a variety of cosmetic, personal care products, and cosmeceutical formulations comprising an effective amount of a block copolymer, ETPEA, and solvent or mixture thereof, necessary to obtain the desired properties. The skilled artisan will be able to determine the effective amount and type of block copolymer film former, ETPEA, solvent or mixture thereof, and additional ingredients desired depending on the application and degree of durability, flexibility, applicability, wearability, uniformity, adhesion, water and oil resistance, transfer resistance, and abrasion resistance, preferably in the absence of irritation. The desired formulation will form a stable cosmetic or cosmeceutical product of sufficient stability such that decomposition or degradation from the preferred or commercialized state does not occur. Moreover, the inventive composition demonstrates the ability to maintain, retain, or prolong a desired effect, such as but not limited to color, moisture, shine, anti-aging, UV protection, and the like.

In another embodiment, the compositions of the disclosure may be used to hold or bind onto the biological surface, topical coatings, actives and/or functional ingredients. The active or functional ingredients may include colorants, pigments, ultraviolet filters, moisturizing agents, fragrances, insecticides, pharmaceutical agents, anti-aging ingredients, and other active or functional ingredients known in the cosmetic or pharmaceutical arts.

In yet a further embodiment, a method of conveying durability, flexibility, oil resistance, water resistance, abrasion resistance, and transfer resistance to a biological tissue, comprising: applying the composition of the instant disclosure having at least a charge-neutral hydrophobic block copolymer and an ETPEA dissolved in a solvent or mixture thereof that is compatible to both the block copolymer and ETPEA, to a biological tissue such as but not limited to the skin, hair, and nails; and drying the applied composition, in an amount effective to convey durability, flexibility, oil resistance, water resistance, abrasion resistance, and transfer resistance by forming a film when the composition is applied to the biological tissue and dried.

This technology and the inventive compositions are applicable to a wide variety anhydrous and powdered products, including but not limited to: foundations, concealers, mascaras, blushes, eyeliners, eyeshadows, face or body powders, as well as skin care products, such as long wearing masks, sun screens and insect repellants. In particular, the composition of the disclosure may include a cosmetic formulation. One embodiment of the disclosure relates to cosmetic foundations, where the formulation of a cosmetic foundation may contain, in addition to the composition of the disclosure, additional thickening agents and emollients in an amount that provides coverage and achieves the other desired properties.

Another embodiment of the disclosure is mascara, which employs the composition of the disclosure and produces increased stability and adherence to keratin surfaces, such as eyelashes. Mascaras using the composition of the disclosure may also provide greater wear resistance, improved water resistance, and improved cosmetic properties.

A further embodiment of the disclosure includes lotions such as suntan lotion or sunblock. Lotions employing the composition of the disclosure may provide increased transfer resistance and water resistance. Lotions using the composition may also provide greater wearability.

Yet another embodiment of the disclosure includes eyeliner and eyeshadow products. Eyeliners and eyeshadows employing the composition of the disclosure may provide increased stability and adherence to eyelid tissue. Eyeliners and eyeshadows using the composition of the disclosure may also provide greater water resistance and improved cosmetic properties.

Another embodiment is a make-up composition for the face employing the composition of the disclosure which provides a homogeneous film that has a light texture and remains comfortable to wear throughout the day. The preferred face make-up is not tacky or sticky, nor does it transfer, migrate, or stain, but is long-lasting, sweat resistant, soft, supple, elastic, flexible, and comfortable on the skin. The make-up composition also conveys a natural or fresh look with flawless coverage.

The packaging of the inventive composition into, for example, a kit or article of manufacture, and application device for any embodiment of the disclosure is chosen and manufactured by persons skilled in the art on the basis of their general knowledge, and adapted according to the nature of the composition to be packaged. Moreover, the type of device to be used may be in particular linked to the consistency of the composition, in particular to its viscosity; it may also depend on the nature of the constituents present in the composition, such as the presence of volatile compounds. The kit or article of manufacture may include, but is not limited to, the inventive composition, a device for the application of the inventive composition, instructions for the use and application of the inventive composition, a listing of ingredients and/or warnings, and the like.

A further embodiment of the disclosure relates to a topical composition in the form of a liquid, gel, foam, cream, lotion, semi-solid, solid, powder, spray, solution, serum, or the like that is a cosmetic, a personal care product, a cosmeceutical or medicinal formulation, an insect repellent, or a sun product, where the composition comprises at least a block copolymer film former, an ETPEA, and a solvent or mixture thereof that sufficiently uniformly dissolves the components. The composition is water resistant, sweat resistant, oil resistant, abrasion or rub resistant, and transfer resistant, flexible, non-tacky, durable, adhesive, provides a moisture barrier, and capable of binding and/or delivering one or more active components, such as but not limited to, a colorant, a dye, a ultraviolet absorber, a moisturizer, a shine enhancer, an anti-aging agent, a biologically active agent, a insecticide/pesticide, and an organic or inorganic active agent. For example, a sunblock composition of the present disclosure is sweat- and water-resistant, including treated swimming pool water, fresh water, and ocean water. The composition is also smudge resistant and does not flake. The composition may be used in products, such as but not limited to, sun care, skin care, color cosmetics, mascaras, hair products (shampoos, conditioners, hairspray, mousses and dyes/colorants), a mascara, a nail enamel, a lip coloring product, a foundation, eye make-up, a skin care product, a personal hygiene product, and a topical drug or active delivery.

Many cosmetic compositions of the disclosure including pigmented cosmetics such as foundations, concealers, mascaras, lipsticks, and other cosmetic, insect repellents, and sunscreen lotions leave soft oily films that can rub off or transfer quite easily. Compositions are therefore capable of becoming deposited, at least in part, by contact onto certain items, such as, for example, a glass, a cup, an item of clothing or the skin. Upon deposition, compositions leave a mark on the item. The result is less than optimal and requires application of the composition to be repeated regularly to compensate for the loss due to the transfer.

Although there are several transfer resistant cosmetic compositions that are known in the art, the instant composition has surprisingly improved upon them such that the desired effect is prolonged, maintained and retained. In view of the properties of the block copolymer and ETPEA which retain the active ingredients, the resulting instant composition has transfer resistance which is better than the prior art compositions. The conventional make-up compositions known in the art which have high transfer resistance generally comprise fatty substances, volatile oils, in particular volatile silicone oils and/or volatile hydrocarbon oils. The majority of these transfer-free compositions, however, are tacky; thus, the application and spreadability of the compositions are not ideal for cosmetics, personal care products, and cosmeceuticals. Example 9 demonstrates the effects of transfer resistance under different conditions (Dry, Water, and Sebum) of the inventive formulation compared to two other formulations.

Besides transfer resistance, compositions must maintain stability. Oftentimes film formers used in the art are mixed with a solvent to function as a thickener. However, the formulations which result can present a problem if the solvent in these thickeners migrate out of the gel matrix as in syneresis causing an instability of the formulation. Therefore, there remains a need for a durable, transfer resistant and stable composition, which also possesses desirable properties, such as but not limited to, ease of application, comfort, flexibility, durability, non tackiness during and after application, abrasion resistance, oil resistance, and water resistance.

The compositions of the disclosure are also effective in providing water resistance. The compositions may thereby minimize the active or functional ingredients from washing off, which is particularly useful in sun products, mascaras, and hair products. The compositions may also retard dehydration of the skin by forming an occlusive film and reducing transepidermal water loss especially in moisturizers.

In a one embodiment, the compositions may provide a film barrier between the skin and the environment, where the film contains the active and/or functional ingredients. The film formed by the composition may increase the activity of the functional ingredients such as the SPF and UV light protection and/or block the effect of the humidity and the environment.

In yet another embodiment, it is preferred that the block copolymer film former and ETPEA be compatible with the other ingredients in the composition. The composition of the disclosure may also include any additive usually employed in the field envisaged such as antioxidants, perfumes, essential oils, stabilizers, cosmetic active substances, moisturizers, vitamins, essential fatty acids, lipophilic sunscreens, liposoluble polymers, and especially hydrocarbon polymers such as polyalkylenes and polyacrylates for improving smoothness or spreadability, water and oil resistance, transfer resistance, or other cosmetic or cosmeceutical properties desired by one of skill in the art.

Non-limiting examples of optionally added ingredients include: emollients, thickening agents, for example, opacifying agents, clays, or organoclays, silicas, cellulose derivatives, plasticizers, gels, oils, olive oils, esters, waxes, solvents, surfactants; hectorites; synthetic polymers such as an acrylic polymer or an associative polymer of the polyurethane type; gums and in particular xanthan gum; spreading agents; dispersants; preservatives, in particular water-soluble preservatives; antifoaming agents; wetting agents; ultraviolet-screening agents; perfumes or fragrances; fillers; cosmetic or pharmaceutical active agents; moisturizers; vitamins and derivatives thereof; and biological materials and derivatives thereof. If the softness and elasticity of the composition are to be increased still further, it is also possible to add a plasticizer which is commonly added for cosmetic materials. Suitable materials may include both low-molecular weight and also high-molecular weight plasticizers which are optionally used, solubilized, or dissolved in a co-solvent.

Suspending and thickening agents typically include waxes, silica gels, gums, clays, fumed silica, fatty acid soaps, and various hydrocarbon gels, and other ingredients that when incorporated into the formulation remain on the surface of keratinous tissues. Waxes include, but are not limited to, natural and synthetic waxes, hydrocarbon-based waxes, fluoro waxes and/or silicone waxes and can be of plant, mineral, animal and/or synthetic origin. In particular, the waxes have a melting point of greater than 25° C., preferably greater than 45° C. The compositions of the present disclosure may contain from 0 to about 30 weight percent waxes by weight of the composition. Waxes are useful in the instant compositions when it is desirable to have a stick formulation as the wax provides structure. Moreover, the waxes are present in a desirable amount that maintains the beneficial effects of the inventive composition.

Non-limiting examples of additional ingredients, such as emollients and conditioners/conditioning materials, conditioners, and conditioning materials, that may preferably be used in the compositions of the disclosure include glycerine, propylene glycol, cyclomethicone, dimethicone, octyldodecanol; olive oil, esters, amodimethicone, dimethicone PEG 8 phosphate, phenyl trimethicone, which is a conditioning material and a shine enhancer, and other similar ingredients disclosed in the International *Cosmetic Dictionary and Handbook*. (Eds. Gottschalck, Tara E., and Gerald N. McEwen. Twelfth ed. Washington, D.C.: The Cosmetic, Toiletry, And Fragrance Association (Now Known As The Personal Care Products Council), 2008. Print) which is hereby incorporated by reference.

Although silicone has frequently been used as an additive to provide flexibility and moisture-resistance in cosmetic formulations, silicone, such as dimethicone, is not an appropriate additive for use in the inventive non-hair compositions, i.e., foundations or skin care products. Whereas, additives comprising silicones with phenyl rings, such as for example, phenyl trimethicone, would be useful in both skin care as well as hair products when combined with the block copolymer/ETPEA gel or solution because of their compatible solubilities.

Another embodiment of the disclosure is directed to ingredients particularly useful in hair products. Since consumers continue to demand hair products that are extra moisturizing, shine enhancing, hair dye retaining, de-frizzing, and the like, additional ingredients are necessary to comply with the demand. The disclosed composition advantageously complexes with these actives thereby forming a film or barrier on the hair to retain these actives. The ingredients typically found in hair care products include but are not limited to surfactants, including anionic or cationic. Non-limiting examples of anionic surfactants include those based on sulfate, sulfonate or carboxylate anions, perfluorooctanoate (PFOA or PFO), perfluorooctanesulfonate (PFOS), sodium dodecyl sulfate (SDS), ammonium lauryl sulfate, other alkyl sulfate salts, sodium laureth sulfate or sodium lauryl ether sulfate (SLES), alkyl benzene sulfonate, soaps, or fatty acid salts. Anionic surfactants are most useful in shampoos while cationic surfactants are preferably in conditioners. However, in some embodiments, quaternary ammonium cations are not required in hair creams, as the skilled formulations artisan understands.

Non-limiting examples of cationic surfactants include those based on quaternary ammonium cations (quats), cetyl trimethylammonium bromide (CTAB) or hexadecyl trimethyl ammonium bromide, other alkyltrimethylammonium salts, cetylpyridinium chloride (CPC), polyethoxylated tallow amine (POEA), benzalkonium chloride (BAC), benzethonium chloride (BZT), and silicone quats.

Other additional ingredients useful in hair care products include, shine enhancers, conditioning materials, preservatives, fragrances, thickeners, emollients, dyes, and the like. Without being bound by theory, the block copolymer and ETPEA gel or solution may play a role in enhancing the efficacy of the surfactant, particularly the quats. Although the surfactants may be used in softening, smoothing, or conditioning, the quats also assist in holding the product on the hair since opposite charges attract, as hair is generally negatively charged while quats are positively charged. Therefore, conditioners are designed to have a positive charge, as we want the hair conditioner to adhere and absorb onto the human hair without leaving deposits. Whereas, shampoos are designed to have a negative charge, in order to prevent the shampoo from adhering or absorbing onto the hair to result in a clean finish. Thus, the combination of the block copolymer and ETPEA, which promote the plasticizing properties, and the quats that provide the retention of ingredients, enables long wear and the desired effect from the active additive.

For colored or pigmented products, the amount of block copolymer, ETPEA, solvent(s), and additional ingredients may be adjusted for maximizing adherence to and water, oil, and transfer resistance from the biological substrate or surface. An important consideration is the ratio of pigments to the amount of block copolymer. A pigment should be understood to mean inorganic or organic, white or colored particles. Coloring agents that may be used in the practice of the disclosure may include pigments, lakes, and dyes which are well known in the art and are disclosed in the *Cosmetic Ingredient Handbook*, First Edition, J. M. Nikitakis, et al., Cosmetic, Toiletry, and Fragrance Association, Washington D.C., 1988, the contents or which are hereby incorporated by reference.

Depending on the application for the composition, pigments may be added to provide color or no color. Non-limiting examples of organic pigments include, FD&C dyes, D&C dyes, including D&C Red, Nos. 2, 5, 6, 7, 10, 11, 12, 13, 30 and 34, D&C Yellow No. 5, Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable coloring agents include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and any other pigment or treated pigment known in the cosmetic arts.

Fillers and mother-of-pearl may also be added to said formulations to modify the texture of the composition and the matte/gloss appearance. Fillers should be understood to mean lamellar or nonlamellar, inorganic or synthetic, colorless or white particles. Mother-of pearl should be understood to mean iridescent particles produced especially by certain mollusks in their shell or else synthesized. Pearling agents that may be used in the practice of the disclosure include mica, iron oxides, titanium dioxide and any other pearling agent known in the cosmetic arts. Non-limiting examples of fillers and microspheres used either alone or in combination, for example, the pressed powder composition prototypes include: talc, corn starch nylon powder, polymethyl methacrylate, polytetrafluorothylene, zinc stearate, boron nitride, calcium silicate, and the like.

Compounds commonly used in the cosmetic arts for preventing or reducing fungal and/or microorganismal growth and preservatives are also useful for addition to the composition of the disclosure. By including these compounds, the shelf life of the composition is lengthened. These anti-fungal and anti-microorganisms include but are not limited to methyl paraben, butyl paraben, sodium dehydroacetate, and the like. Caprylyl glycol, phenoxyethanol, phenoxyethanol, methylparaben, ethylparaben, n-butylparaben, propylparaben, isobutylparaben, and the like or blends thereof are non-limiting examples of useful preservatives for addition to the disclosed compositions.

Although some of these materials may include an oily feeling and increased spreadability, as observed with some esters and organic sunscreens, the overall composition of the disclosure maintains its desired properties of transfer resistance, abrasion resistance, water, sweat and oil resistance, durability, flexibility, applicability, wearability, uniformity, sheen or gloss, drying time, adhesion, preferably in the absence of irritation. The person skilled in the art will of course take care to choose the optional additional compounds and/or their quantities in such a way that the advantageous properties of the composition according to the disclosure are not, or are substantially not, impaired by the envisaged addition(s). In embodiments where these materials are added to the formulations of the disclosure to enhance the spreadability and the emollience of the product, however, it is preferred that the above materials be present in low enough concentrations for the formulation to retain its desired properties. These ingredients may be selected variously by the person skilled in the art in order to prepare a composition which has the desired properties, for example, consistency or texture. The choice of block copolymer film former, additional ingredients, and their concentrations may also be adjusted to vary the desired properties.

The contents of all patents, patent applications, published PCT applications and articles, books, references, reference manuals and abstracts cited herein are hereby incorporated by reference in their entirety to more fully describe the state of the art to which the disclosure pertains.

As various changes may be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings.

EXAMPLES

The following examples further describe and demonstrate embodiments within the scope of the present disclosure. The examples are given solely for the purpose of illustration and are not to be constructed as limitations of the present disclosure, as many variations thereof are possible without departing from the spirit and scope of the disclosure.

Example 1

Block Copolymer/ETPEA Gel

Table 1 provides exemplary block copolymer/ETPEA gel formulas. Briefly, the block copolymer and ETPEA gel compositions were prepared by mixing all of the ingredients identified in Table 1 in a jacketed type, sealed mixing unit with side sweep blade mixing capacity (Eurostar-labortechnik; IKA Works Inc; Wilmington, N.C.). Heat all of the ingredients at 95° C. for 6 hours using a programmable heating unit setting at 95° C. plus/minus 5° C. at 500 to 2000 rpm until everything is uniformly dissolved. Cool down mixture with slow mixing below 500 rpm and final temp less than about room temperature or 25° C.

The solvent was selected from isododecane, isohexadecane, isopropyl palmitate, myristyl palmitate, or combinations thereof. The block copolymer was a block copolymer selected from styrene-isobutylene-styrene; styrene-ethylene-styrene; styrene-ethylene-propylene-styrene; or combinations thereof. The ETPEA was a bis-stearyl ethylenediamine/neopentyl glycol/stearyl hydrogenated dimer dilinoleate copolymer.

TABLE 1

BLOCK COPOLYMER/ETPEA GEL FORMULAS

| Ingredients | 1 | 2 | 3 | 4 |
|---|---|---|---|---|
| Solvent | 84 | 87 | 88 | 89 |
| Block copolymer | 14 | 9 | 6 | 3 |
| ETPEA | 2 | 4 | 6 | 8 |
| Total Weight Percent | 100 | 100 | 100 | 100 |

Example 2

Foundation Compositions

Table 2 provides foundation composition formulas based on the block copolymer and ETPEA gel described in Example 1 above. Table 3 provides foundation composition formulas additionally utilizing phenyl trimethicone. Briefly, Phase A (SIBS/ETPEA of Example 1 or SIBS/ETPEA/phenyltrimethicone of Table 3) were prepared by the method of Example 1. The mixture was then stirred while slowly cooled to about 25° C. The resulting soft gel was then used for preparing the foundation compositions by adding additional ingredients typically used in cosmetic formulations.

The preformed soft gel of Phase A was mixed with Phase B of Table 2 or 3 and heated to about 60° C. followed by the addition of Phase C until homogenous. The mixture was then slowly cooled down to room temperature under constant stirring.

TABLE 2

FORMULAS FOR FOUNDATION COMPOSITIONS

| Ingredients | 1 | 2 | 3 | 4 |
|---|---|---|---|---|
| Phase A: | | | | |
| Block copolymer/ETPEA gel | 38 | 34 | 28 | 20 |

TABLE 2-continued

FORMULAS FOR FOUNDATION COMPOSITIONS

| Ingredients | 1 | 2 | 3 | 4 |
|---|---|---|---|---|
| Phase B: | | | | |
| Solvents | 23 | 27 | 26 | 28 |
| Emulsifiers | 1 | 3 | 5 | 7 |
| Rheology Modifiers | 2 | 4 | 7 | 10 |
| Other Polymers | 1 | 2 | 3 | 5 |
| Phase C: | | | | |
| Fillers/Microspheres | 30 | 25 | 26 | 25 |
| Pigments | 5 | 5 | 5 | 5 |
| Total Weight Percent | 100 | 100 | 100 | 100 |

TABLE 3

FORMULAS FOR FOUNDATION COMPOSITIONS

| Ingredients | 1 | 2 | 3 | 4 |
|---|---|---|---|---|
| Phase A: | | | | |
| Block copolymer/ETPEA gel | 38.0 | 34 | 28 | 20 |
| Phenyl Trimethicone | 0.5 | 1.0 | 5.0 | 10.0 |
| Phase B: | | | | |
| Solvents | 22.5 | 26 | 21 | 18 |
| Emulsifiers | 1 | 3 | 5 | 7 |
| Rheology Modifiers | 2 | 4 | 7 | 10 |
| Other Polymers | 1 | 2 | 3 | 5 |
| Phase C: | | | | |
| Fillers/Microspheres | 30 | 25 | 26 | 25 |
| Pigments | 5 | 5 | 5 | 5 |
| Total Weight Percent | 100 | 100 | 100 | 100 |

Example 3

Pressed Powder Composition Prototype

Table 4 provides pressed powder composition formulas based on a block copolymer and ETPEA composition. Briefly, the Phase A ingredients were premixed and heated to a temperature as described in Example 1 until a clear, uniform gel or solution resulted. In a separate vessel, the pressed powder compositions were prepared by blending the Phase B ingredients. The Phase A solution was slowly dispersed into Phase B under constant agitation at about 500 rpm to about 2000 rpm at a temperature of about 190° F. or about 87.8° C. The combined Phases were mixed at high speed of about 500 rpm to about 2000 rpm for about 30 minutes. The resulting mixture was then run though a jet mill twice (Model #02-512, Serial #1303; The Jet Pulverizer Company; Palmyra, N.J.) until a fine powder having a particle size of about 10 microns to about 20 microns (where the average particle size was about 15 microns) was achieved. The resulting fine powder was then pressed into the appropriate packaging to present a pressed powder composition.

Although any of the block copolymers previously described could have been used, a block copolymer selected from styrene-isobutylene-styrene; styrene-ethylene-styrene; styrene-ethylene-propylene-styrene; or combinations thereof, was utilized in the pressed powder composition. Moreover, the ETPEA exemplified herein was a bis-stearyl ethylenediamine/neopentyl glycol/stearyl hydrogenated dimer dilinoleate copolymer.

TABLE 4

FORMULAS FOR PRESSED POWDER COMPOSITIONS

| Ingredients | 1 | 2 | 3 | 4 |
|---|---|---|---|---|
| Phase A: | | | | |
| Block copolymer | 4 | 3 | 2 | 1 |
| ETPEA | 0.1 | 0.2 | 0.3 | 0.5 |
| Solvents | 15.9 | 14.8 | 14.7 | 13.5 |
| Phase B: | | | | |
| Fillers/Microspheres | 75 | 77 | 78 | 80 |
| Anti-fungal/microorganisms | | | | |
| Pigments | 5 | 5 | 5 | 5 |
| Total Weight Percent | 100 | 100 | 100 | 100 |

Example 4

Lip and Eye Compositions

Tables 5-8 provide lip and eye composition formulas based on the block copolymer and ETPEA gel described in Example 1 above. Tables 9 and 11 provide lip and eye compositions additionally utilizing phenyl trimethicone. Briefly, the compositions were prepared by stirring and heating at about 105° C. for 15 minutes or until homogeneous, 7% styrene-isobutylene-styrene (SIBS) in isododecane of Phase A. In a separate vessel, the Phase B ingredients were premixed and heated to a temperature of about 190° F. or about 87.8° C. for 3 hours or until a clear, uniform solution resulted. The Phase B solution was slowly dispersed into Phase A under constant agitation at about 500 rpm to about 2000 rpm at a temperature of about 190° F. or about 87.8° C. The combined Phases were mixed at high speed of about 500 rpm to about 2000 rpm for about 30 minutes. The resulting mixture was then run though a jet mill twice (Model #02-512, Serial #1303; The Jet Pulverizer Company; Palmyra, N.J.) until a fine powder having a particle size of about 10 microns to about 20 microns (where the average particle size was about 15 microns) was achieved.

Although any of the block copolymers previously described could have been used, a block copolymer selected from styrene-isobutylene-styrene; styrene-ethylene-styrene; styrene-ethylene-propylene-styrene; or combinations thereof, was utilized in the pressed powder composition. Moreover, the ETPEA exemplified herein was a bis-stearyl ethylenediamine/neopentyl glycol/stearyl hydrogenated dimer dilinoleate copolymer.

TABLE 5

FORMULAS FOR LIPSTICK AND EYESTICK COMPOSITIONS

| Ingredients | 1 | 2 | 3 | 4 |
|---|---|---|---|---|
| Phase A: | | | | |
| Block copolymer/ETPEA gel | 38 | 34 | 28 | 20 |
| Phase B: | | | | |
| Solvents | 23 | 27 | 26 | 28 |
| Emulsifiers | 1 | 3 | 5 | 7 |
| Rheology Modifiers | 2 | 4 | 7 | 10 |
| Other Polymers | 1 | 2 | 3 | 5 |

TABLE 5-continued

FORMULAS FOR LIPSTICK AND EYESTICK COMPOSITIONS

| Ingredients | 1 | 2 | 3 | 4 |
|---|---|---|---|---|
| Phase C: | | | | |
| Waxes | 30 | 25 | 26 | 25 |
| Pigments | 5 | 5 | 5 | 5 |
| Total Weight Percent | 100 | 100 | 100 | 100 |

TABLE 6

FORMULAS FOR LIPSTICK AND EYESTICK COMPOSITIONS

| Ingredients | 1 | 2 | 3 | 4 |
|---|---|---|---|---|
| Phase A: | | | | |
| Block copolymer/ETPEA gel | 38 | 34 | 28 | 20 |
| Phenyl Trimethicone | 0.5 | 1.0 | 5.0 | 10.0 |
| Phase B: | | | | |
| Solvents | 22.5 | 26 | 21 | 18 |
| Emulsifiers | 1 | 3 | 5 | 7 |
| Rheology Modifiers | 2 | 4 | 7 | 10 |
| Other Polymers | 1 | 2 | 3 | 5 |
| Phase C: | | | | |
| Waxes | 30 | 25 | 26 | 25 |
| Pigments | 5 | 5 | 5 | 5 |
| Total Weight Percent | 100 | 100 | 100 | 100 |

TABLE 7

FORMULAS FOR LIP AND EYE GEL COMPOSITIONS

| Ingredients | 1 | 2 | 3 | 4 |
|---|---|---|---|---|
| Phase A: | | | | |
| Block copolymer/ETPEA gel | 38 | 34 | 28 | 20 |
| Phase B: | | | | |
| Solvents | 38.0 | 39.5 | 39 | 40.5 |
| Emulsifiers | 1 | 3 | 5 | 7 |
| Rheology Modifiers | 2 | 4 | 7 | 10 |
| Other Polymers | 1 | 2 | 3 | 5 |
| Phase C: | | | | |
| Waxes | 15 | 12.5 | 13 | 12.5 |
| Pigments | 5 | 5 | 5 | 5 |
| Total Weight Percent | 100 | 100 | 100 | 100 |

TABLE 8

FORMULAS FOR LIP AND EYE GEL COMPOSITIONS

| Ingredients | 1 | 2 | 3 | 4 |
|---|---|---|---|---|
| Phase A: | | | | |
| Block copolymer/ETPEA gel | 38 | 34 | 28 | 20 |
| Phenyl Trimethicone | 0.5 | 1.0 | 5.0 | 10.0 |
| Phase B: | | | | |
| Solvents | 37.5 | 38.5 | 34 | 30.5 |
| Emulsifiers | 1 | 3 | 5 | 7 |
| Rheology Modifiers | 2 | 4 | 7 | 10 |
| Other Polymers | 1 | 2 | 3 | 5 |
| Phase C: | | | | |
| Waxes | 15 | 12.5 | 13 | 12.5 |
| Pigments | 5 | 5 | 5 | 5 |
| Total Weight Percent | 100 | 100 | 100 | 100 |

Example 5

Hair Formulation Compositions

Table 9 provides hair composition formulas based on the block copolymer and ETPEA composition described herein. Briefly, the hair compositions are prepared by combining the ingredients of Phase A and heating at a temperature ranging from about 116° C. to about 122° C. in a mineral oil bath. The ingredients are mixed until uniform and dissolved at medium speed. This generally takes a minimum of 7 hours to dissolve. The batch can be prepared the following day by reheating the premix A in a water bath of about 74° C. to about 78° C. until liquid, and slow mixing until uniform. Phase A is cooled and the ingredients of Phase B are added one at a time at a temperature of about 64° C. to about 66° C. The mixture is mixed at slow speed until uniform. Phase C is added at a temperature of less than 49° C. and mixed at a slow speed until uniform. Phase D is added to the batch at a temperature of less than or equal to about 43° C. The resulting solution is typically used in hair formulations.

TABLE 9

FORMULAS FOR HAIR COMPOSITIONS

| Ingredients | 1 | 2 | 3 |
|---|---|---|---|
| Phase A: | | | |
| Block copolymer | 4.5 | 4.5 | 2.5 |
| ETPEA | 0.1 | 0.1 | 5 |
| Solvent | 87.7 | 87 | 76.5 |
| Emollients/Conditioners | 3.4 | 3.4 | 3 |
| Phase B: | | | |
| Phenyl Trimethicone | 2 | 2 | 5 |
| Conditioner | 0.25 | 2 | 4 |
| Cationic Surfactant | 1 | 0 | 4 |
| Phase C: | | | |
| Preservative | 1 | 1 | 0 |
| Phase D: | | | |
| Fragrance | 0.05 | 0 | 0 |
| Total Weight Percent | 100 | 100 | 100 |

Example 6

Hair Shine Serum Compositions

Table 10 provides a specific hair shine serum compositions based on the block copolymer and ETPEA described herein. Briefly, the hair serum is prepared by combining the ingredients of Part A and heating at a temperature ranging from about 116° C. to about 122° C. in a mineral oil bath. The ingredients are mixed until uniform and dissolved at medium speed. At this point the Part A mixture may be checked to confirm complete dissolution. This generally takes a minimum of 7 hours to dissolve. The completed batch can be prepared the following day by reheating the premix A in a water bath of about 74° C. to about 78° C. until liquid, and slow mixing until uniform. Part A is cooled to a temperature of about 74° C., and the ingredients of Part B are added one at a time at a temperature of about 64° C. to about 66° C. The mixture is mixed at slow speed until uniform. Part C is added at a temperature of less than 49° C. and mixed at a slow speed until uniform. Part D is added to the batch at a temperature of less than or equal to about 43° C. The resulting solution is typically used in hair formulations for shine.

TABLE 10

FORMULA FOR HAIR SHINE SERUM COMPOSITIONS

| Ingredients | 1 | 2 |
| --- | --- | --- |
| Phase A: | | |
| Block copolymer | 4.5 | 4.5 |
| ETPEA | 0.1 | 0.1 |
| Solvent | 87.7 | 84.7 |
| Thickener | 0.4 | 0.4 |
| Phase B: | | |
| Shine enhancer/Conditioner | 5 | 5 |
| Cationic Surfactant | 1 | 0 |
| Conditioning Material | | 4 |
| Phase C: | | |
| Preservative | 1 | 1 |
| Phase D: | | |
| Fragrance | 0.3 | 0.3 |
| Total Weight Percent | 100 | 100 |

Example 7

Consumer Comparison of Long Wear Foundation Compositions

In a consumer test survey, consumers were asked to compare the inventive foundation composition comprising the SIBS and ETPEA (Combined foundation) to a commercialized transfer resistant, long wearing foundation composition (Standard) which does not contain the combination of SIBS and ETPEA.

Each of the 32 consumer testers applied a layer of each foundation composition onto different clean (i.e., without wearing any face products) halves of their faces (e.g., left side vs. right side) in a double blind test. The consumers were asked to compare the feel, comfort, appearance/coverage, and ease of removal of each at different times: initially after application, at 8 hours, and up to 9.9 hours after application and answer questions in a questionnaire comparing the two foundation compositions. Data were tabulated using the Compusense5 program and analyzed using the IFPrograms (2-AFC, delta module).

The comments from the consumer tests described above indicated that overall, the Combined foundation composition comprising a block copolymer and ETPEA provided a significantly more natural look upon initial application, as well as after 8 hours of wear compared to the other Standard foundation. The consumers found that the feel of the Combined foundation was significantly more lightweight and comfortable upon initial application and at 8 hours after application when compared to the Standard. The consumers thought that the Combined foundation was breathable and comfortable. As for the appearance or coverage, the consumers agreed that the Combined foundation evened out skin tone, reduced the appearance of lines and wrinkles, reduced redness, and reduced the appearance of age or sun spots. Overall, the inventive Combined foundation provided a natural and flawless appearance. Finally, with respect to the ease of removing the foundation compositions, the consumers found that the Combined foundation composition was easier to remove than the Standard foundation.

The technical evaluator who oversaw the consumer testing determined that the Combined foundation was more visible and provided more coverage at hours after application than the Standard foundation. On average, the Combined foundation lasted 9.9 hours. The technical evaluator deemed the Combined foundation composition to be "long wearing."

Example 8

Consumer Testing of Long Wear Foundation Composition

In a consumer test survey, consumer testers were asked to evaluate the inventive foundation composition comprising the SIBS and ETPEA. Each of the 32 consumer testers applied a layer of the foundation composition onto their clean faces (i.e., without wearing any face products). The consumers were asked to evaluate the feel, comfort, application, appearance, and coverage at different times: initially at application and after 8 hours of application and answer questions. The questionnaire comprised of a series of questions about the aesthetics and performance of the foundation based on a seven point attribute scale. An Expert Evaluator also rated the appearance and wear properties at the initial time point and after 8 hours of wear. Data were tabulated using the Compusense5 program and analyzed using the IFPrograms (2-AFC, delta module).

Overall, the consumers liked the composition initially and after 8 hours of wear. They found that the foundation was easy to apply and blend, providing even coverage and a smooth feel upon application. They found that the composition was initially lightweight; evened out skin tone; reduced: the appearance of fine lines and wrinkles, appearance of redness, dark under eye circles, age/sun spots, and shine; improved the appearance of skin texture; and provided a flawless and natural look. While after 8 hours of wear, the foundation was found to be breathable and comfortable. The finish, coverage, and color were maintained after 8 hours of wear. The foundation composition was found to still control shine and oil breakthrough, while appearing freshly applied. After 8 hours the consumers found that the foundation did not settle in lines, wrinkles or pores, nor look cakey or masky. Even though the foundation did not transfer after 8 hours, the significant majority of the consumers found that the foundation composition was easy to remove.

Example 9

Transfer Resistance of Foundation Compositions

The transfer resistance of the foundation composition described in Example 2 was examined in comparison to the two other foundation compositions using the transfer resistance testing protocol described below. The two other foundation compositions were made with either 1) only a block copolymer (10% SIBS gel) or 2) with only an ETPEA (10% polyamide gel); whereas, the foundation of Example 2 was made with both a block copolymer and an ETPEA. The testing protocol used herewith is described below.

Transfer Resistance Test Method

This method was used to determine the transfer of foundation as conducted in three different manners: dry, water, and sebum/oil. Generally, one milliliter of each of the foundation compositions was deposited on three different collagen films and allowed to dry for 24 hours at room temperature. For the water transfer test, the foundation films were further sprayed with water (~1 ml) and allowed to sit for 1 minute at room temperature. For the sebum/oil transfer test, the foundation films were further sprayed with artificial sebum (1 ml) and allowed to sit for 1 minute at room temperature. The artificial sebum was prepared as described by Stig E. Friberg and David W. Osborne (*JAOCS*, 63(1):123-126 (January 1986), incorporated herein by reference.

The transfer process was conducted by sliding a piece of cotton cloth attached to and underneath a 2 kilogram weight over each of the foundation films using a new piece of cloth for each test. The amount of foundation that transferred to the cotton cloth was observed and visually analyzed for comparison.

Transfer Resistance Test Results

Qualitatively, the order of transfer for each of the three conditions were found to be as follows: For the dry foundation film, the foundation having both SIBS and ETPEA was found to have transferred less than either of the foundations having either ETPEA or SIBS alone. These single element foundations had about the same level of transfer to each other, but both transferred more foundation than the combined SIBS and ETPEA foundation.

To test the resistance of water on each of the foundation films that had water sprayed, the foundations having both SIBS and ETPEA or ETPEA alone were found to transfer less than the foundation with SIBS alone.

Finally, the foundation films sprayed with artificial sebum resulted in approximately the same transfer resistance for all three foundation types as summarized in Table 11.

TABLE 11

COMPARISON OF THE AMOUNT OF TRANSFER

| CONDITION | FOUNDATION TYPES |
| --- | --- |
| DRY | SIBS + ETPEA < ETPEA alone, SIBS alone |
| WATER | SIBS + ETPEA, ETPEA alone < SIBS alone |
| ARTIFICIAL SEBUM | SIBS + ETPEA = ETPEA alone = SIBS alone |

Example 10

Measuring Shine in Hair Composition

In order to test whether the disclosed hair compositions of Table 10 adds mirror-like shine without stickiness or weighing hair down; has a shine that lasts all day or until the next shampoo, or refreshes and revives dull, dry looking hair equipment from Bossa Nova was used to measure shine. Instrument results were based on the principle of using polarized illumination with a polarizing camera that is able to separate polarized light that is reflected from a surface (specular) and unpolarized light that scatters (diffuse light). The more specular light, the more shine on hair or lips. Measurements were conducted on blond hair swatches comprised of human hair from International Hair Importers.

The method to measure shine is based on image analysis. The visual impression of shine is largely due to two mechanisms, i.e., reflection and diffusion of light. Hair reflects incoming light like a mirror and can also diffuse it. The reflection mechanism preserves incoming polarization (parallel polarization) and diffusion creates crossed polarization. Measuring both amounts of light allows the quantification of shine by software and patented camera design.

The imaging system instrumentation is a technology that allows for the quantitation of shine on hair swatches by quantitating shine in vivo (or on real models in real time), or by visually comparing shine products by gloss mapping. There are two set-up configurations; one to measure hair swatches on a cylinder and the other to measure hair with a special face or lighting.

The shine band is the shiny section of hair focused under the camera lens. Once the hair was positioned on the cylinder, the region of interest was measured by the software. Band width is measured by Bossa Nova software and allows for the percentage shine to be calculated.

Luster data were obtained by integrating areas under the curves from specular and diffused light. The amount of luster was calculated by comparing the untreated tress luster value to the treated tress luster value. Specifically, Luster is calculated by the formula: $P/(C \times W)$. P is amount of specular light; C is diffused light (area under curve); and W is width of specular peak.

The shine was simply calculated by the formula: $[(\text{Treated Value} - \text{Untreated Value})/\text{Untreated Value}] \times 100$. The calculated percentage represented the percent increase in shine. The hair treated with the disclosed shine hair product produced greater than 90% more shine versus untreated hair. Even more than 8 hours later, the treated hair produced a significant shine benefit.

What is claimed is:

1. A cosmetic composition, comprising:
   a charge-neutral, hydrophobic block copolymer and an ester-terminated polyesteramide polymer dissolved in at least one solvent,
   wherein the charge-neutral, hydrophobic block copolymer is styrene-isobytylene-styrene (SIBS) copolymer present in an amount ranging from about 0.01 weight % to about 50% weight % based on the total weight of the composition,
   wherein the ester-terminated polyesteramide polymer is a bis-stearyl ethylenediamine/neopentylglycol/stearyl hydrogenated dimer dilinoleate copolymer present in an amount ranging from about 0.01 weight % to about 50% weight % based on the total weight of the composition, and
   one or more of: film formers, emulsifiers, rheology modifiers, polymers, fillers, coloring agents, cosmetic vehicles, microspheres, or active or inactive ingredients,
   wherein said composition is free of tackifier resin.

2. The composition of claim 1, wherein the solvent is isododecane, isohexadecane, isopropyl palmitate, polyglycerol diisostearate, pheynyl trimethicone, or combinations thereof.

3. The cosmetic composition of claim 1, wherein the cosmetic composition is a foundation, a pressed powder, a powder foundation, a face powder, a concealer, a blush, an eye shadow, a loose powder, a powder blush, a talc powder, a cream, a lotion, a skin care product and/or a personal care product.

4. A cosmetic composition, comprising:
a styrene-isobutylene block copolymer,
  wherein the styrene-isobutylene block copolymer is styrene-isobytylene-styrene (SIBS) copolymer present in an amount ranging from about 0.01 weight % to about 50% weight % based on the total weight of the composition,
and
a bis-stearyl ethylenediamine/neopentyl glycol/stearyl hydrogenated dimer dilinoleate copolymer dissolved in a solvent of isododecane, isohexadecane, isopropyl palmitate, isopropyl myristate, or combinations thereof, present in an amount ranging from about 0.01 weight % to about 50% weight % based on the total weight of the composition, wherein said composition is free of tackifier resin.

5. A hair composition, comprising:
a charge-neutral, hydrophobic block copolymer wherein the charge-neutral, hydrophobic block copolymer is styrene-isobytylene-styrene (SIBS) copolymer present in an amount ranging from about 0.01 weight % to about 50% weight % based on the total weight of the composition, and
an ester-terminated polyesteramide polymer dissolved in at least one solvent, wherein the ester-terminated polyesteramide polymer is a bis-stearyl ethylenediamine/neopentylglycol/stearyl hydrogenated dimer dilinoleate copolymer present in an amount ranging from about 0.01 weight % to about 50% weight % based on the total weight of the composition,
wherein said composition is free of tackifier resin.

6. A method of preparing a cosmetic composition, comprising:
(a) mixing and heating until homogeneous a composition comprising:
  (i) a charge neutral, hydrophobic block copolymer, wherein the charge-neutral, hydrophobic block copolymer is styrene-isobytylene-styrene (SIBS) copolymer,
  (ii) an ETPEA polymer, wherein the ETPEA polymer is a bis-stearyl ethylenediamine/neopentylglycol/stearyl hydrogenated dimer dilinoleate copolymer present in an amount ranging from about 0.01 weight % to about 50% weight % based on the total weight of the composition,
  (iii) a solvent or mixture thereof, and
  (iv) one or more of: emulsifiers, rheology modifiers, or polymers, wherein said composition is free of tackifier resin;
(b) mixing and heating the homogenous mixture and one or more of: fillers, microspheres, or coloring agents until homogeneously dispersed;
(c) milling the homogeneously dispersed mixture until the fillers, microspheres, and coloring agents are uniformly dispersed; and
(d) cooling the uniformly dispersed mixture, thereby forming the cosmetic composition.

\* \* \* \* \*